(12) United States Patent
Belloso

(10) Patent No.: US 6,580,013 B1
(45) Date of Patent: Jun. 17, 2003

(54) INEXPENSIVE DIAPER WETNESS MONITORING SYSTEM

(76) Inventor: Gregorio M. Belloso, 5302 Chinaberry Dr., Salisbury, MD (US) 21801

( * ) Notice: Subject to any disclaimer, the term of this patent is extended or adjusted under 35 U.S.C. 154(b) by 0 days.

(21) Appl. No.: 10/042,116

(22) Filed: Jan. 10, 2002

(51) Int. Cl.$^7$ ................................................. A61F 13/15
(52) U.S. Cl. .................. 604/361; 200/61.04; 200/61.05
(58) Field of Search ........................... 604/361; 340/573, 340/604; 200/61.05, 61.04

(56) References Cited

U.S. PATENT DOCUMENTS

| | | | |
|---|---|---|---|
| 4,191,950 A | | 3/1980 | Levin et al. |
| 4,205,672 A | | 6/1980 | Dvorak |
| 4,212,295 A | | 7/1980 | Snyder |
| 4,356,818 A | | 11/1982 | Macias et al. |
| 4,539,559 A | | 9/1985 | Kelly et al. |
| 4,939,504 A | * | 7/1990 | Miller ......................... 340/604 |
| 5,144,284 A | * | 9/1992 | Hammett .................. 340/573.1 |
| 5,903,222 A | * | 5/1999 | Kawarizadeh et al. ....... 340/604 |
| 5,959,535 A | * | 9/1999 | Remsburg ................... 340/604 |
| 6,160,198 A | * | 12/2000 | Roe et al. .................... 604/361 |
| 6,200,250 B1 | * | 3/2001 | Janszen ....................... 493/383 |
| 6,301,978 B1 | * | 10/2001 | Sargent ................... 73/862.49 |
| 6,384,296 B1 | * | 5/2002 | Roe et al. .................... 604/361 |
| 6,464,635 B1 | * | 10/2002 | Jimenez Cerrato et al. . 600/362 |
| 6,479,727 B1 | * | 11/2002 | Roe .............................. 604/361 |
| 2002/0019615 A1 | * | 2/2002 | Roe et al. .................... 604/361 |
| 2002/0145525 A1 | * | 10/2002 | Friedman et al. ........ 340/573.5 |

* cited by examiner

Primary Examiner—Weilun Lo
Assistant Examiner—Michael G. Bogart
(74) Attorney, Agent, or Firm—Norman B. Rainer

(57) ABSTRACT

A wetness monitoring system for a disposable diaper includes an elongated compliant sensor installable within the front portion of the diaper and having an inner conductive layer, a hydrophilic porous middle layer containing a water-soluble ionizable salt, and an outer conductive layer. The several layers are non-conductively interbonded at discontinuous sites. The upper extremity of the sensor provides electrical connector terminals. When urine contacts the sensor, the salt dissolves to form a highly conductive volume of solution that causes an electrical short circuit between inner and outer layers. The short circuit enables a low voltage direct current to activate an alarm mechanism.

7 Claims, 4 Drawing Sheets

INEXPENSIVE DIAPER WETNESS MONITORING SYSTEM

BACKGROUND OF THE INVENTION

1. Field of the Invention

This invention relates to diapers equipped with a wetness monitoring system.

2. Description of the Prior Art

Babies and incontinent adults need to have their diapers changed when they are wet and soiled, not only for hygienic reasons, but to prevent diaper rash, dermatitis and ulcerations which can lead to serious infections.

Various types of diaper wetness monitors have previously been disclosed. For example, U.S. Pat. No. 4,356,818 to Macias et. al. describes an electric moisture-sensing disposable diaper having a liquid impervious outer sheet, a liquid permeable inner lining, and a moisture absorbing wadding associated with one or two strips of electrically conductive material. The presence of moisture produces an electrical short circuit which activates an alarm device.

U.S. Pat. No. 4,212,295 to Snyder discloses a moisture-responsive pad for treatment of enuresis. The pad employs two conductive outer layers separated by a non-conductive central layer, and is not adapted for use inside a disposable diaper.

U.S. Pat. No. 4,205,672 concerns a sensing device employing a conductive layer within a diaper. The baby's skin serves as a second conductor. A signalling device is activated when the conductors are short-circuited by urine.

U.S. Pat. No. 4,191,950 describes a sensor consisting of a double strip of specially manufactured conductive vinyl cloth connected to specialized silver-impregnated Velcro fasteners. The sensor is designed to survive repeated laundering, and is intended primarily as an anti-bed-wetting device to train enuretic children to overcome bed wetting.

U.S. Pat. No. 4,539,559 to Kelly et. al. discloses a disposable warning device for detecting urine-wet undergarments. It employs a disposable sensor circuit having separated electrical terminals which may be printed on an absorbent pad. Its voltage source may be a 9 volt battery. Current passes between said terminals when wet with urine. The requisite operational current may produce discomfort to the wearer.

The moisture-detecting devices of the aforesaid Patents are of questionable reliability because they rely on the conductivity of the wetting substance itself (urine or other liquid wastes) in order to function properly. The problem with this is that there is high variability in the conductive efficiency of these fluids. Their conductance varies not only with the concentration of the dissolved solutes but also with the degree to which these substances are converted to their ionized forms. The colloidal or semi-colloidal nature of urine also affects its conductance. Thus, when the urine is highly dilute its conductance is reduced to nearly that of water, making it less reliable for activating these devices.

It is accordingly an object of the present invention to provide a wetness monitoring system suitable for use in disposable pediatric and adult diapers.

It is another object of this invention to provide a monitoring system as in the foregoing object which can reliably detect diaper wetness regardless of the conductance of the urine or other liquid bodily waste.

It is a further object of the present invention to provide a monitoring system of the aforesaid nature whose voltage requirement is sufficiently low so as to avoid discomfort or injury to the patient.

It is a still further object of this invention to provide a monitoring system of the aforesaid nature amenable to sufficiently low cost manufacture as to be commercially suitable for integration into disposable diapers, or for retrofitting into standard commercially available diapers.

Yet another object of the present invention is to provide a monitoring system of the aforesaid nature which enables a remotely stationed caregiver or supervisor to be aware not only of the status of the diaper but also of the timing and frequency of diaper changes and to have an automatic and permanent record of the same.

These objects and other objects and advantages of the invention will be apparent from the following description.

SUMMARY OF THE INVENTION

The above and other beneficial objects and advantages are accomplished in accordance with the present invention by a wetness monitoring system for a disposable diaper comprising:

a) a compliant sensor installable within the front center portion of said diaper and comprised of an inner conductive layer, a hydrophilic porous middle layer containing a water-soluble ionizable salt, and an outer conductive layer, said layers being non-conductively interconnected at discontinuous sites, said sensor being elongated between a lower extremity, and an upper extremity providing connection terminals, b) a source of low voltage direct current electricity, and c) an alarm pack containing electrically activatable alarm means and electrical circuitry interactive between said terminals, electricity, and alarm means, whereby d) said middle layer, when contacted by urine, releases said salt to form a highly conductive volume of solution that produces an electrical short circuit between said inner and outer layers to activate said alarm means.

A telemetry sender unit may be interactively associated with said alarm pack to produce a recordable signal at a distant location.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
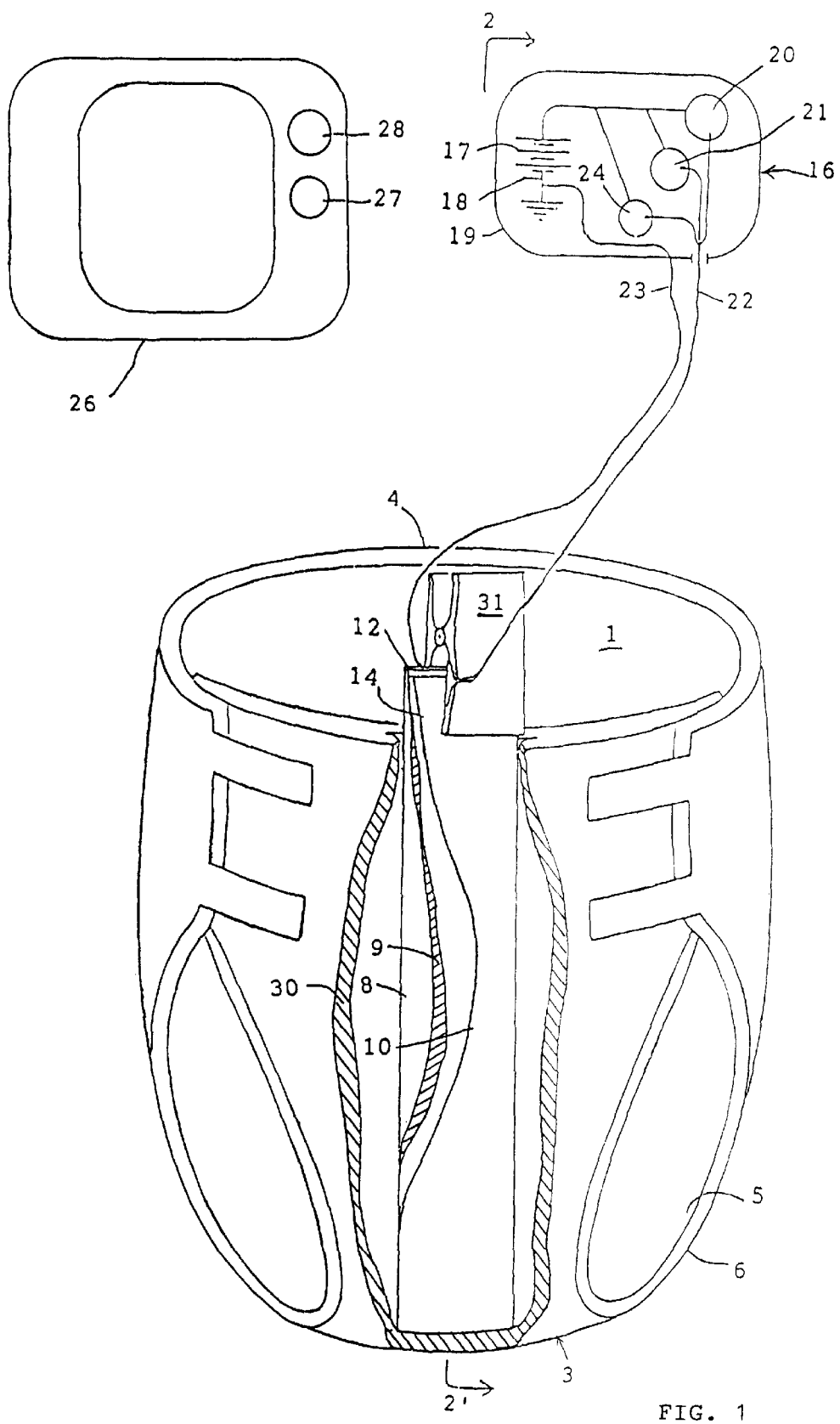
FIG. 1 is a front view, partly in section, of a diaper equipped with the wetness monitoring system of the present invention.
Figure 2:
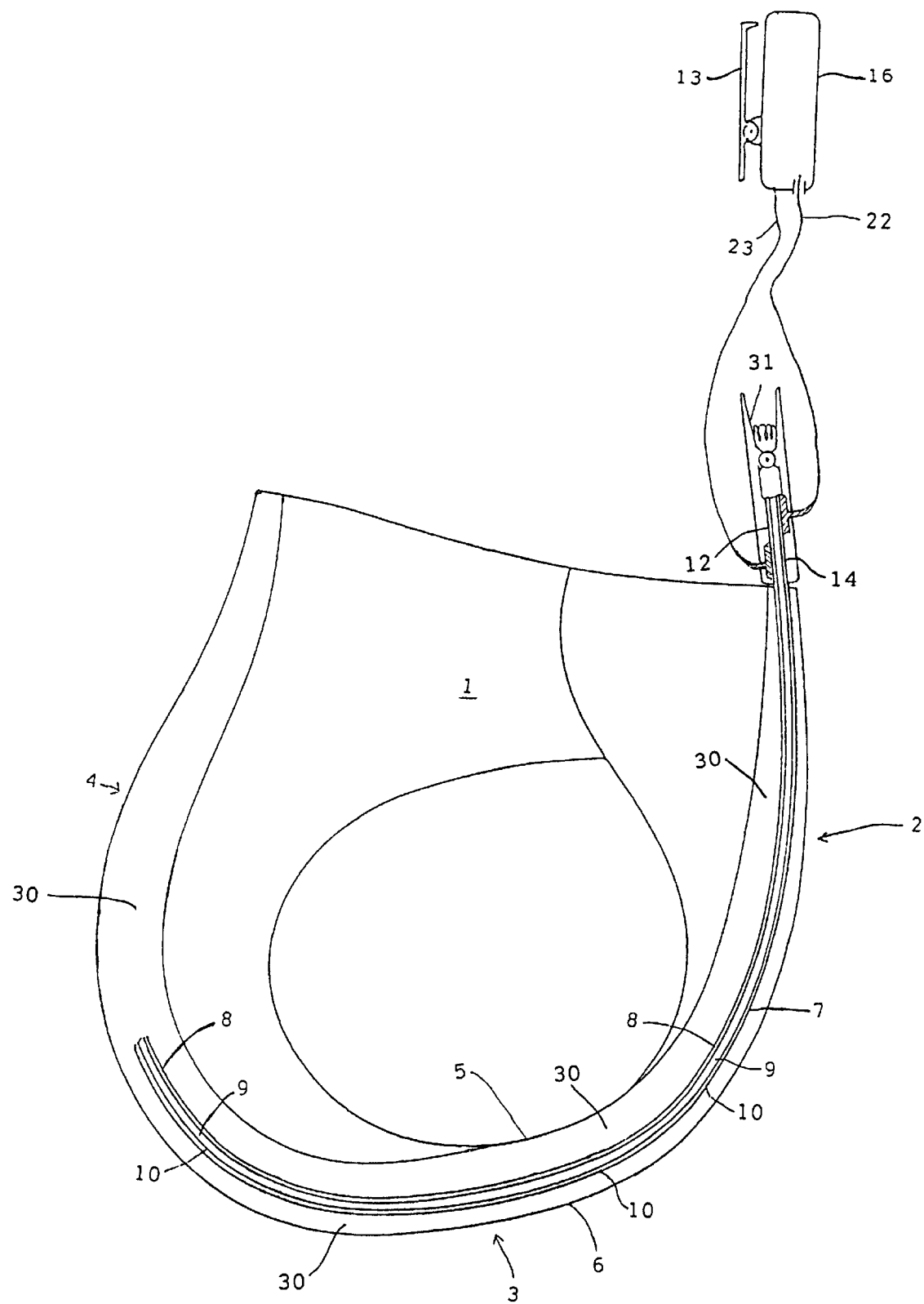
FIG. 2 is a side sectional view along line 2—2' of FIG. 1.

Referring now to FIGS. 1–4, there is shown a diaper 1 with a front portion 2, a middle portion 3, a rear portion 4, a porous inner lining 5 and a non-porous outer lining 6. A thick absorbent layer 30 lies between inner lining 5 and outer lining 6. A long wetness sensor 7 is disposed within the absorbent layer 30 extending substantially from front to back along the midline of the diaper 1. The wetness sensor 7 is comprised of an inner conductive layer 8, a hydrophilic porous middle layer 9, and an outer conductive layer 10, said layers bonded together as a unit by discontinuous droplets of non-conductive adhesive material. The wetness sensor 7 extends beyond the frontal upper edge of the diaper 1 so that the extended part of conductive layer 8 becomes the inner conductive layer terminal 12, and the extended part of outer conductive layer 10 becomes the outer conductive layer terminal 14.

The alarm pack 16 contains a battery 17 whose negative terminal 18 is grounded to the casing 19 and whose positive terminal is connected to visible signal means 20 and to audible signal means 21. The alarm pack 16 has a grounded external negative terminal 23 and an insulated external positive terminal 22 to which the positive poles of the visible signal means 20 and audible signal means 21 are connected. Negative terminal 23 and positive terminal 22 are connected through a releasable connecting means 31, in the form of a clip biased to close, to inner conductive layer terminal 12 and outer conductive layer terminal 14, respectively.

When the inner conductive layer terminal 12 is connected to the external negative terminal 23 of alarm pack 16, and the outer conductive layer terminal 14 is connected to the external positive terminal 22 of alarm pack 16, the battery 17 causes an electric charge potential to form between the inner conductive layer 8 and the outer conductive layer 10 in the wetness sensor unit 7. Although the inner conductive layer 8 and the outer conductive layer 10 are in fairly close proximity to each other no current will flow because they are separated from each other by non-conductive middle layer 9.

Middle layer 9 is highly wettable and is impregnated with a highly soluble and highly ionizable salt, such as sodium chloride. When the wetness sensor unit 7 is wet with a water-based fluid such as urine or diarrheic stool, the sodium chloride content of layer 9 goes into solution, producing a volume of solution which is highly conductive of electricity and which is disposed in a zone between said inner and outer layers. Said conductive zone closes the circuit between the inner conductive layer 8 and the outer conductive layer 10, causing electricity to flow. The visible signal means 20 and audible signal means 21 are thereby activated, thus indicating to the caregiver that the diaper is wet.

Alarm pack 16 has a clip 13 so that it may be placed on an exposed part of the patient's clothing or bedding so as to be more easily seen by caregivers. The external negative terminal 23 and the external positive terminal 22 of alarm pack 16 are in the form of a spring loaded clip for easy connection and disconnection with the wetness sensor terminals. The alarm pack 16 is not disposable but the wetness sensor 7 is integral to the diaper 1 and is disposable along with it. Conductive layers 8 and 10 may be comprised of aluminum foil. Porous layer 9 may be comprised of absorbent paper material.

Figure 3:
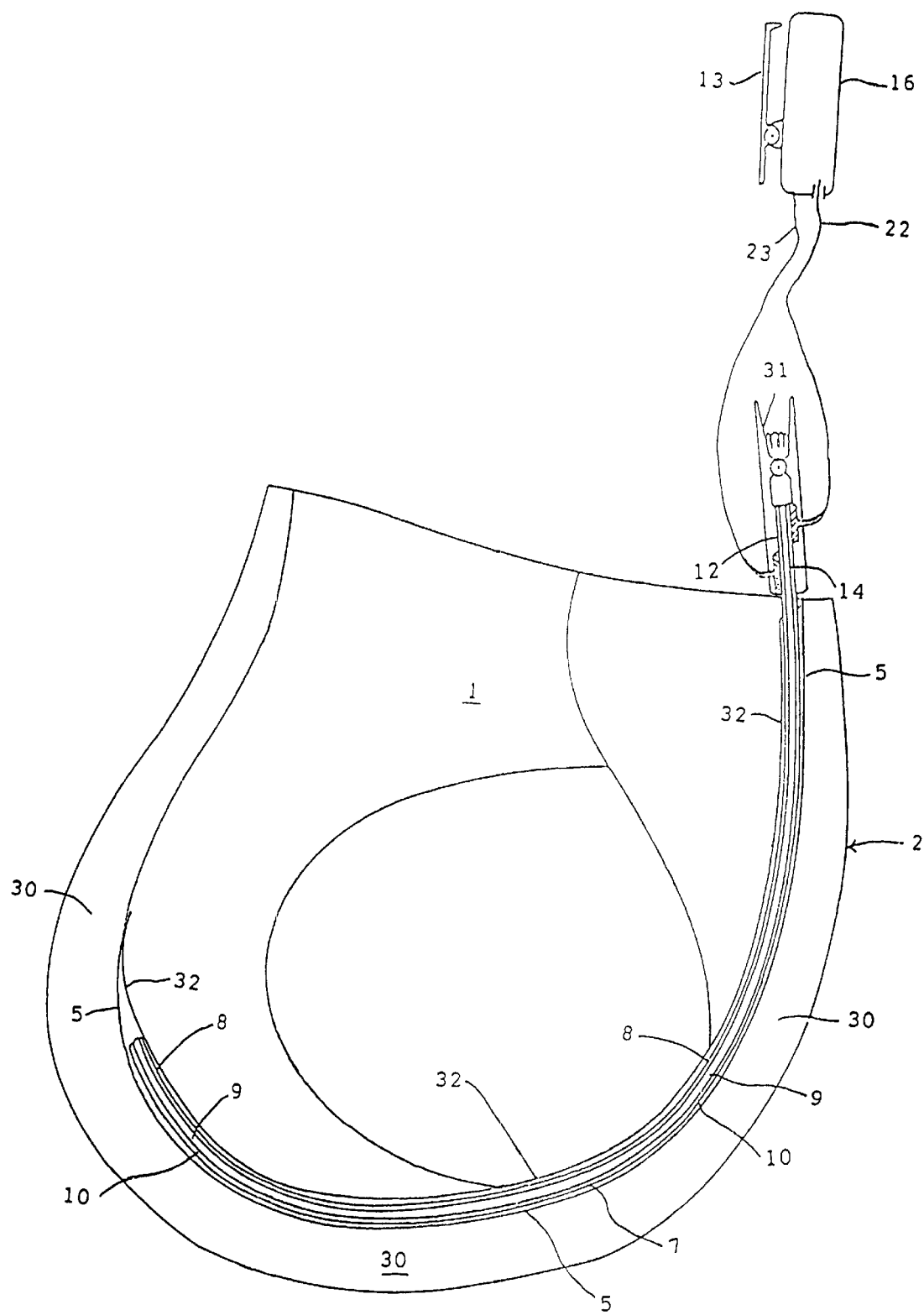
FIG. 3 is a side sectional view similar to FIG. 2 of an alternative embodiment showing the wetness sensor retrofitted into the inner surface of a standard diaper.

In FIG. 3, the wetness sensor 7 is fitted with a porous adhesive backing 32 with which it is affixed to the inner lining 5 of diaper 1. In this manner the wetness sensor 7 can be retrofitted to any existing diaper for wetness monitoring purposes.

Figure 4:
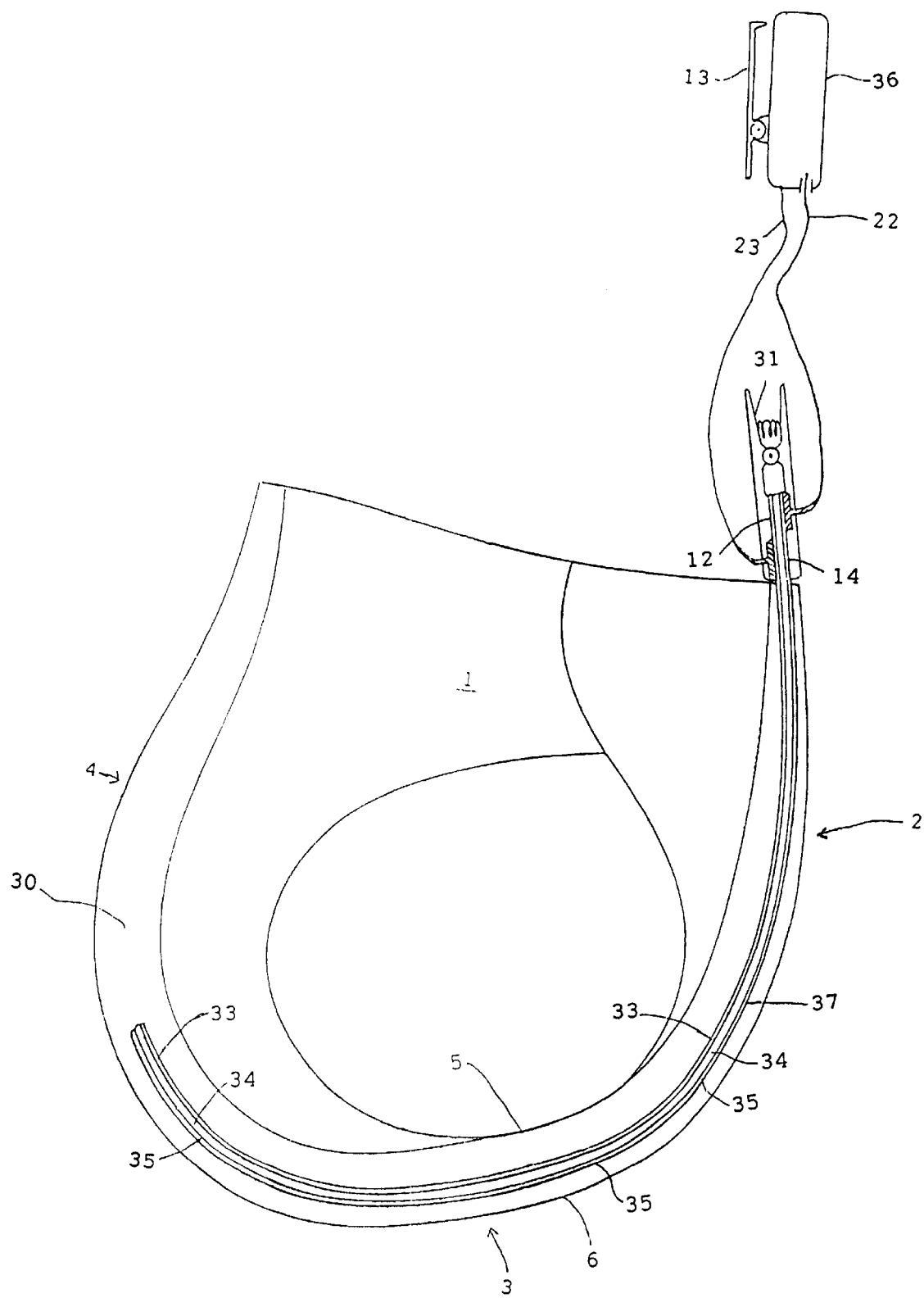
FIG. 4 is a sectional view similar to FIG. 2 showing a second alternative embodiment where the sensor unit itself becomes a source of electrical potential similar to a voltaic cell when it is wet with an aqueous solution.

A second alternative embodiment is shown in FIG. 4 where the sensor unit itself produces electric current when it is wet with water or an aqueous solution such as urine. This is based on the fact that, when electrodes of two different materials such as zinc and copper are immersed in an electrolytic solution, one electrode acquires a positive charge and the other electrode acquires a negative charge. When the two electrodes are connected externally by a conductive circuit, current will flow.

Returning now to FIG. 4, inner conductive layer 33 is made of a suitable material such as copper, and outer conductive layer 35 is made of a different material such as zinc. The hydrophilic porous middle layer 34 is impregnated with a suitable electrolytic powder. When wetness sensor 37 is wet with urine or other aqueous solution, the electrolytic powder in porous layer 34 will go into solution to produce a highly conductive liquid zone. Such action produces opposing charges in the conductive layers 33 and 35 so that electric current will flow through terminals 12, 23, 14 and 22 to alarm unit 36 which is especially designed to detect said current and emit a visible or audible signal.

In some applications, it is preferred that the system allows the supervisors to more closely monitor how soon the patients are attended to after the wetness alarm is activated. For this purpose, an optional telemetry sender unit 24 in the alarm pack 16 may be provided for transmitting audio and visual signals and other data to a remote display receiver unit 26, which may be placed in the nurses' station, through a wired circuit or a wireless system. The receiver unit 26 may be equipped with a buzzer 27, a signal light 28, a data storage means such as semiconductor chips, and suitable electrical connection means for transmitting stored data to a computer for hard copy or subsequent retrieval.

Although these preferred embodiments are described in great detail it is to be understood that various changes and modifications may be made therein without departing from the spirit and scope of the invention which is more fully defined in the appended claims.

Having thus described my invention, what is claimed is:

1. A disposable diaper having an associated wetness monitoring system, said diaper having front and rear portions, a porous inner lining, non-porous outer lining and absorbent center layer disposed between said inner and outer linings, said wetness monitoring system comprising:
   a) a compliant long sensor positioned at said front portion and comprised of an inner conductive layer, a non-conductive porous middle layer impregnated with a water-soluble ionizable salt, and an outer conductive layer, said layers being non-conductively interconnected at discontinuous sites by a bonding agent, said sensor being elongated between a lower extremity and an upper extremity providing connection terminals, said sensor being disposable with said diaper, and
   b) an alarm pack releasably attachable to said connection terminals and containing:
      i) a battery which supplies low voltage direct current electricity,
      ii) electrically activatable means for producing an alarm signal, and
      iii) electrical circuitry interactive between said terminals, battery and electrically activatable means, whereby
   c) said middle layer, when contacted by urine, releases said salt to form a highly conductive volume of solution that produces an electrical short circuit between said inner and outer layers to produce said alarm signal.

2. The diaper of claim 1 wherein said sensor is disposed within said absorbent center layer.

3. The diaper of claim 1 wherein said sensor is attached by way of a porous adhesive backing to the inner lining of said diaper.

4. The diaper of claim 1 further comprising a telemetry sender interactively associated with said alarm pack to transmit a recordable electrical signal to a distant location.

5. The diaper of alarm 1 wherein said hydrophilic porous middle layer is comprised of cellulose-based paper.

6. The diaper of claim 1 wherein said alarm pack is provided with spring-urged clip means which achieve releasable attachment to said connection terminals.

7. The diaper of claim 1 wherein said salt is sodium chloride.

* * * * *